(12) United States Patent
Leen

(10) Patent No.: US 8,347,478 B2
(45) Date of Patent: Jan. 8, 2013

(54) METHOD AND SYSTEM FOR REPLACING THE WATER COOLED LASER IN A MICROPLATE READER

(76) Inventor: Thomas Leen, Raleigh, NC (US)

(*) Notice: Subject to any disclaimer, the term of this patent is extended or adjusted under 35 U.S.C. 154(b) by 435 days.

(21) Appl. No.: 12/693,091

(22) Filed: Jan. 25, 2010

(65) Prior Publication Data

US 2010/0313403 A1 Dec. 16, 2010

Related U.S. Application Data

(60) Provisional application No. 61/146,832, filed on Jan. 23, 2009.

(51) Int. Cl.
*B23P 6/00* (2006.01)

(52) U.S. Cl. .................................................. 29/402.01

(58) Field of Classification Search ............... 29/402.01, 29/402.03, 402.08; 356/327
See application file for complete search history.

(56) References Cited

U.S. PATENT DOCUMENTS

| 5,355,215 A | 10/1994 | Schroeder et al. |
| 7,265,829 B2 | 9/2007 | Jiang et al. |
| 2010/0319177 A1* | 12/2010 | Leen ......................... 29/402.01 |

* cited by examiner

*Primary Examiner* — John C Hong
(74) *Attorney, Agent, or Firm* — James G. Passé; Passé Intellectual Property, LLC

(57) ABSTRACT

The present invention relates to a method of refurbishing a microplate reader such as a FLIPR type microplate reader by the replacement of the water cooled laser with an LED source which provides a relatively homogeneous light and operating performance comparable to the laser light source.

17 Claims, 3 Drawing Sheets

METHOD AND SYSTEM FOR REPLACING THE WATER COOLED LASER IN A MICROPLATE READER

This application claims priority of U.S. provisional application 61/146,832 filed on Jan. 23, 2009 and is included herein in its entirety by reference.

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

1. Field of the Invention

The present invention relates to a method and system for replacing a lighting system in a microplate reader with a new light source. Specifically the present invention relates to a system which can be used to replace a water cooled laser with an LED light system in an existing microplate reader.

2. Description of Related Art

The use of fluorescence analytical monitoring techniques is well known. Fluorescence measurements can be taken by shining a light source of a first wavelength and then when the sample of light is absorbed the test material is induced to emit light of a second wavelength. Measurement of the second wavelength light, either as length or intensity or the like, can be used to correlate the activity in a cell that is producing the secondary fluorescence. Physiological parameters can then be determined based on the results, such as potassium or other ion channel activity. Florescence type measurements are of great importance to the research and development of new pharmaceutical compositions and are used to screen a variety of tissues for interaction with most any chemical composition that is of interest in affecting the measurable systems.

Typically in the analysis of cells, a variety of older machines are available for using this type of technique with 96 or 384 well multiple well plates. These machines provide a multiwall plate holder, a water cooled laser light source and some form of a receiving camera for detecting the cell second wavelength light emissions. The cells are cultured in each of the wells at the bottom with a growth medium provided over the growing cells. The chemical compound to be tested or otherwise assayed is played into the liquid in each well with the florescent material and the effect measured by excitation by the laser and reading by the camera. For example, in U.S. Pat. No. 5,355,215 to Schroder et al issued Oct. 11, 1994 there is disclosed a method for aligning a camera and a light source for measuring the second wavelength with a minimum about if interference from the supernate liquid. This process has been utilized extensively and appears in later machines and in more recently issued patents, for example in U.S. Pat. No. 7,265,829 issued Sep. 4, 2007 to Jiang et al.

The older machines that utilized water cooled lasers, while difficult to use, were well built and very cost effective. Such machines include the Flipr2® and Flipr3® microplate readers. These machines suffered from the difficulty of using and operating water cooled lasers, but because parts were relatively accessible for repair a burgeoning business in repair and refurbishment developed to keep these machines in service. Since the refurbishment of even a patent product is allowable, repair has been accomplished not only by OEMs but a variety of small companies also repair these types of machines.

Newer machines are very costly and tend to be large in an attempt to avoid the difficulties in using water cooled lasers. An example is the Flipr$^{tetra}$® made by the same company as the older machine, Molecular Devices (MDC). In order to encourage business for themselves MDC has declined to support its older machines and encourages users of the older machines to upgrade. However, for many users the older machines are fine and there is a desire in the marketplace to continue refurbishing these machines. The fact that water cooled lasers that these machines were built to utilize are expensive, hard to use and getting scarce to fit the existing machines, has suggested the repair life of these machines is limited in spite of the desire of users to continue using the machines to the end of their useful life.

LED's are well known and can be obtained in both regular and high output varieties. However, as a light source multiple LEDs tend to produce a non-homogeneous light and while the availability of machines made from scratch and designed to be used with LED light sources has been accomplished, the use of LEDs in machines not designed for this type of light source has been avoided in retrofit situations because of the problems in providing proper lumen intensity, homogeneousity and coverage in a machine designed for an entirely different type of light source.

BRIEF SUMMARY OF THE INVENTION

The use of argon water cooled lasers has been extensively used by microplate readers. These lasers are sensitive and easily misaligned. The microplate readers used with them were designed, shaped and calibrated specifically to be used with these types of lights sources. It has been discovered that it is possible to replace the light source with an LED source under specific conditions and repair such a unit with the appropriate LEDs, filter's holders supports, and the like of the present invention, thus extending the useful repair life of these older microplate readers without the problems normally associated with LEDs and accommodating the design of the older units.

DETAILED DESCRIPTION OF THE INVENTION

Figure 1:
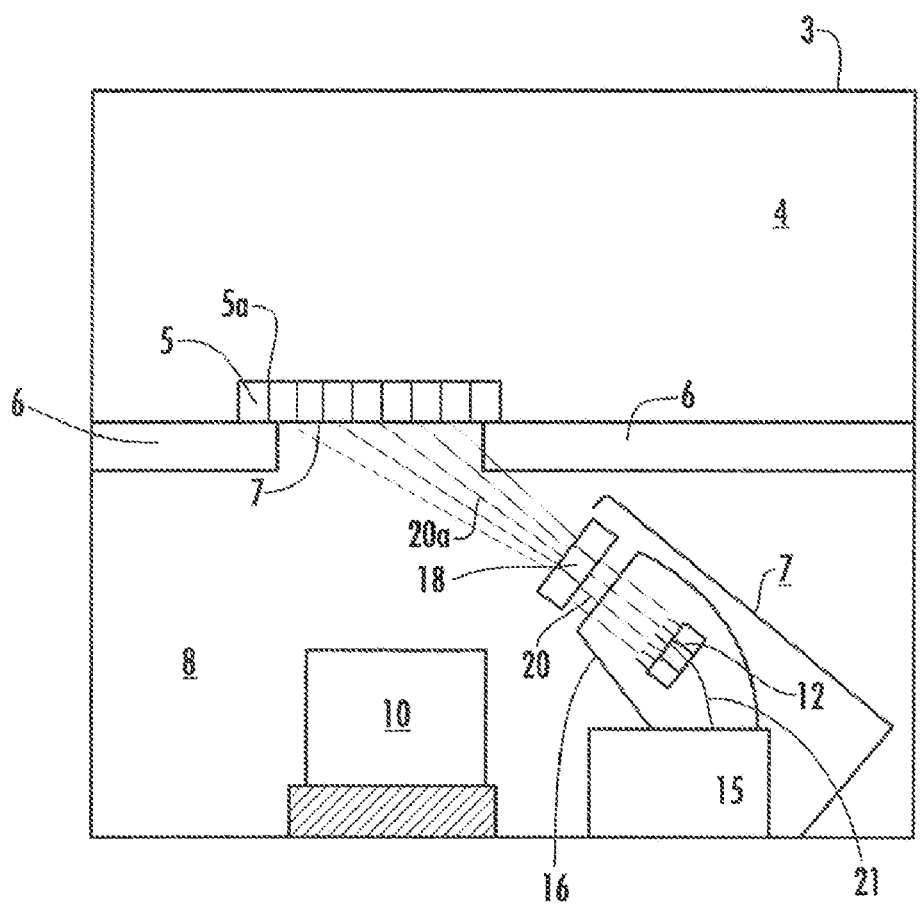
FIG. 1 is a side view of replacement LEDs positioned to shine directly on the bottom of a microplate.

While this invention is susceptible to embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein and specifically describes embodiments in order for those skilled in the art to practice the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are for the purpose of illustrating certain convenient embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein a "fluorescence microplate reader" refers to those microplate readers which originally were designed to handle 384 plate readers or less and use a water cooled laser such as an argon water cooled laser to provide an excitation light source. Argon lasers provide a light of a wavelength of about 488 nanometers. Units such as the FLIPR2 and FLIPR3 unit made by MDC are examples of the intended microplate readers that are repaired using the method and system of the present invention. While the argon lasers do work for their intended purpose in these types of microplate readers, they are difficult to use, have a long warm up time and need to be frequently adjusted. When replacing the lasers during the repair or refurbishment process it is understood that the laser would be removed before beginning with the method and system of the present invention. These types of microplate readers have an upper portion where pipetting is done to a microplate sitting or placed in the reader. Once a microplate is placed in the reader the bottom surface of the microplate is exposed to the bottom portion of the reader where a light source such as the argon laser can shine on the bottom surface of the plate specifically so that it shines on each well bottom surface. Light emissions from the microplate wells occurs in the lower position as well and reaches a CCD type camera either directly or indirectly by any of one or more mirrors.

As used herein the phrase "one or more LED lights" refers to one or more light emitting diodes of a selected color or mixture of colors and having a final output wavelength as well as a light intensity measured in lumens. The minimum amount of luminosity for the LEDs of the invention to work as a replacement is at least sufficient lumens to reach the recommended light intensity for the particular unit the LEDs will replace light in. In one embodiment, the light output is more than 20 lumens and in yet another it is about 300 lumens or more. Any type of LEDs can be used but because high output LEDs can be used in this situation one embodiment includes these high output LEDs. One embodiment has about 5 watt output LEDs. Various colors with various wavelengths can be used also having a variety of lumen outputs. For example, high output LEDs from Edison Opto Corporation of Taiwan produces a blue LED of 50 lumens a warm white of 110 lumens and a white LED of about 160 lumens.

This can be accomplished by as many LED's as is necessary to achieve the minimum taking into account the various outputs of LED lights available. There might be in one embodiment 6 blue high output LED lights but more or less meeting the above criteria is within the scope of the invention. It has also been discovered that a more homogeneous lighting can be achieved by filtering the light or passing the light through a light reducing aperture. In this embodiment lumen output needs to be more than necessary and the proper amount is reduced to the proper level with the filter or aperture. This embodiment provides a more even lighting on the bottom of a microplate during reading and thus when tested, results in a coefficient of variation (CV) of 0.6% or about the same as a water cooled laser. One skilled in the art and understanding the problems described herein can vary the choice of LEDs and filters or apertures to optimize the light source in view of the disclosure herein.

The LED lights need to be held in relative fixed relationship so that light emanating from the one or more LEDs remains constant within the beam produced. The holder can keep the relative position of the LEDs between each other constant but must be able to be adjusted when in place in order to focus the LEDs relative to a microplate bottom that the LEDs are shining on. By mounting the holder on a support the LEDs can be adjusted in three dimensional space relative to the microplate bottom surface. One can easily fashion such adjustment means within the scope of the invention based on the disclosure herein and such is well within the skill in the art. The LED's can be fixedly attached to such support or they can be set by gravity or other means on the support as desired. The fixed method of attaching to a support does allow the support and LEDs to be placed as a unit within the reader and thus makes replacement and set up much quicker and simpler.

In one embodiment the LED's are further contained within a case such as a box or the like. Such case would have a single opening in a single direction. This stray light for the LEDs would be minimized and result in less overall light "noise" in reading the results of experiments with the LED based reader. Since scattered light has been discovered to be a potential problem with the present invention where such is a problem additional dark or black or the like material can be positioned around the inside of the reader as desired to reduce the bounce light effect from the LEDs of the invention.

In order to change the light wavelength to the wavelength the reader needs, or more particularly the cells within a microplate need, to fluoresce. One must position a light filter which changes the wavelength of the LED emissions to the desired wavelength. Where one is attempting to duplicate the argon water cooled laser, a filter which will cause the wavelength to change to 488 nanometers would be used. Typical pass filters are in the 480 to 550 nanometer range but can easily be chosen by one skilled in the art based on the selection of the LED and the desired end wavelength in view of this disclosure. Other wavelengths as desired could be obtained with appropriate filters. Such filters are available in the art. The luminosity is always decreased when passing through a filter and such must be considered and the luminosity matched to the particular filter since each filter may filter out more or less of the luminosity of the original LED lights. The size of the filter is sufficient to allow the LED light to pass entirely through the filter. Restricting the size of the filter can be used to focus and homogenize the emitted light as desired and the size of the desired filter and the distance from the LEDs while critical to the practice of the invention can be determined with minimum experimentation by one skilled in the art in view of this disclosure. One embodiment has the filter attached to the LED case or in another embodiment attached to or supported by the support that supports the LED lights.

The LED lights must, when replaced, shine such that the filtered light shines on the bottom surface of a microplate placed in the reader. This can be done from an angle (less than 90 degrees) as taught by the art cited above or in other embodiments shining at 90 degrees directly or by way of a bounce mirror. The bounce mirror in some embodiments can be a dichroic mirror which allows the filtered LED light to bounce off the dichroic mirror and hit the bottom surface of the microplate reader. Then when the emitted light comes from the bottom surface of the microplate it can pass through the dichroic mirror as long as the angles are correct for use of such a mirror. Therefore, in one embodiment a dichroic mirror that bounces light at 45 degrees is used. Filtered light from the LED bank of lights hits the mirror at 45 degrees and is reflected to the bottom surface of a microplate in the reader. The emitted light from the microplate exits at 90 degrees, passes through the dichroic mirror and to the CCD camera in the reader. This can be seen as discussed with the figures which follow.

The support for the LEDs and optionally the filter or dichroic mirror serves at least two purposes. First, it keeps the parts in relative position to one another and makes 3 dimensional adjustments easier without changing their relative positions. Second, the support allows the system to be placed in an individual reader in such a way that it is immediately positioned for use by positioning the support in the predetermined position. This forgoes the problems of finding the optimum position for each component and then doing the final 3D micro adjustments necessary to align and focus the light. The complete support can be placed into the reader and attached thereto and the installation is essentially complete with only final adjustment calibrations necessary. This embodiment, either with or without the dichroic filter embodiment, allows for quick easy repair, easy adjustment and a lower cost to repair than either replacing the laser or starting with each individual component.

Lastly, it has been discovered that this system can be turned on and off as the laser was using essentially the same means within the reader. Such is surprising since the units were not designed to accept anything other than water cooled argon laser light sources.

Now referring to the drawings. FIG. 1 is a system according to the present invention wherein the LEDs are positioned at an angle to the bottom of a microplate. In the example is shown the inside front view of microplate reader 3. The upper interior is where the microplate 5 is placed and where the reader can perform operations on the contents of the microplate 5 which are positioned in wells 5a. Microplate 5 sits on microplate support 6 and exposes the bottom surface 7 of microplate 5 to lower chamber 8. The laser light in the original FLIPR type reader shines on the bottom 7 and the Fluorescence light shines down from the bottom 7 to mirror 10 and off to a camera (not shown or replace in the present system). The system 1 of the present invention consists of LEDs in a holder 12 and positioned on support 15 which gives the LEDs 11 the correct height, and position and allows the LEDs 11 to be placed as a unit within the reader 3 without need for customizing each installation. The LEDs are also shown within box 16, which while shown as transparent is opaque and preferably of a non-reflective dark color such as black or other appropriate color. A wavelength filter 18 in filter holder 19 is depicted and at an appropriate distance from the LEDs 11 to create the proper wavelength as well as beam spread pattern. The filter is shown as small but as seen in other figures, one can size the filter according to costs and needs of the filter as well as positioning requirements of the filter. The filter holder can be attached to the box or otherwise the entire system interconnected such that the system can be inserted into a microplate reader 3 as a single piece. The LEDs 11 and filter 18 can be in holders which give three dimensional degrees of freedom, the so called six degrees of freedom so that final minute focusing of the light and filter can be done with the system and refocused as necessary after installation. In one example the LED's 11 are six blue high output LEDs from Edison Opto part EDEB-5lax having a 50 lumen output and are filtered in one embodiment by a 485df20 filter of 50 mm in diameter. The filtered light has a wavelength of 480 to 550 nanometers. The LEDs 11 are angled in this embodiment at about 45 degrees from the bottom 7 of the microplate. Other angles are possible within the skill in the art. Light 20 from the LEDs 11 shines on filter 18 and light of a new wavelength 20a emerges and directly strikes the bottom 7 of microplate 5 for excitation of any contents in wells 5a.

One tremendous advantage of the present system 1 is that the entire unit can easily replace the laser of the unit by placement of the system in the open compartment the lower chamber 8 of the microplate reader as a single unit. It has been discovered that when LED's 11 are connected via wire 21 to the controls of microplate reader 3 that a light system which does not have all the frailty of the previous laser light source. It is also determined that such can be accomplished without the need to rebuild the reader 3 and mere refurbishment is possible. One will note that the original mirror 10 remains in place and as such the camera which reads fluorescence from the microplate 5 does not need to be adjusted or removed. Within the space given one can fit the system 1 of the unit in place and either have the components pre-adjusted or individually adjust the LED 11 position and filter 18 position relative to one another. By providing a support 15 it is possible to eliminate the need to constantly adjust the height of the LED system 1 relative to the bottom 7.

Figure 2:
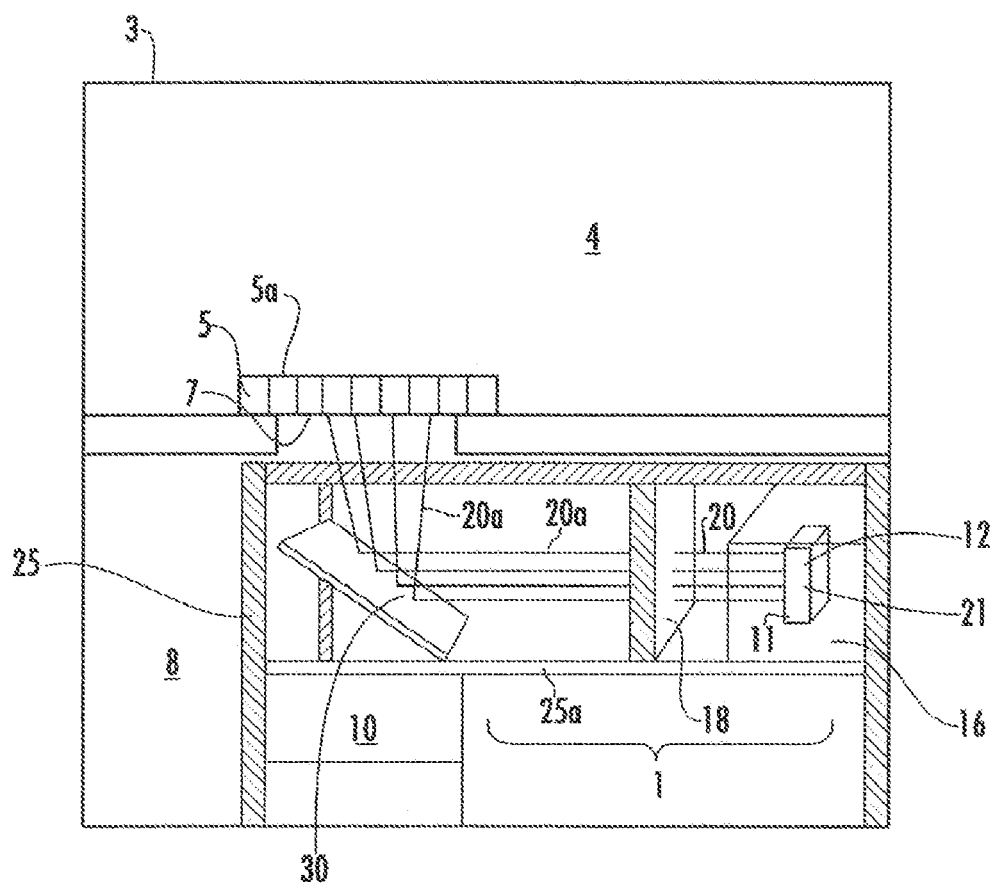
FIG. 2 is a side view of replacement LEDs positioned to shine by bounce mirror.

FIG. 2 involves a separate embodiment of the present invention where it is desirous to shine the LED light at 90 degrees rather than 45 in the previous embodiment. In this embodiment, the system 1 consists of frame 25 which acts as the support 15 did in FIG. 1. The frame 25 has cross members 25a which support the various parts of the system 1 and allow the entire system to be positioned inside the reader 3 in the lower interior 8. In order to utilize a 90 degree light in this embodiment use of a dichroic mirror 30 is used. The dichroic mirror 30 is positioned at a 45 degree angle or as needed. Light shining from the LED's 11 shine through filter 18 and hit mirror 30 reflecting up and hitting bottom 7 at 90 degrees. Reflected light can pass directly though the dichroic filter 30 and hit original reflective mirror 10 in the normal manner to reach the camera (once again not shown). This has the advantage of once again being positioned in a single framed support system and the additional advantage of using a direct beam and not an angled 45 degree beam such as the embodiment in FIG. 1. The cross supports 25a allow for greater flexibility in 6 degree of freedom adjustments than the other embodiment and can accommodate larger filters with ease. Note that while the container 16 is shown as a non-reflective insert other positions on the system or within the lower compartment 8 can be added to the system if particular reflectance becomes a problem.

Figure 3:
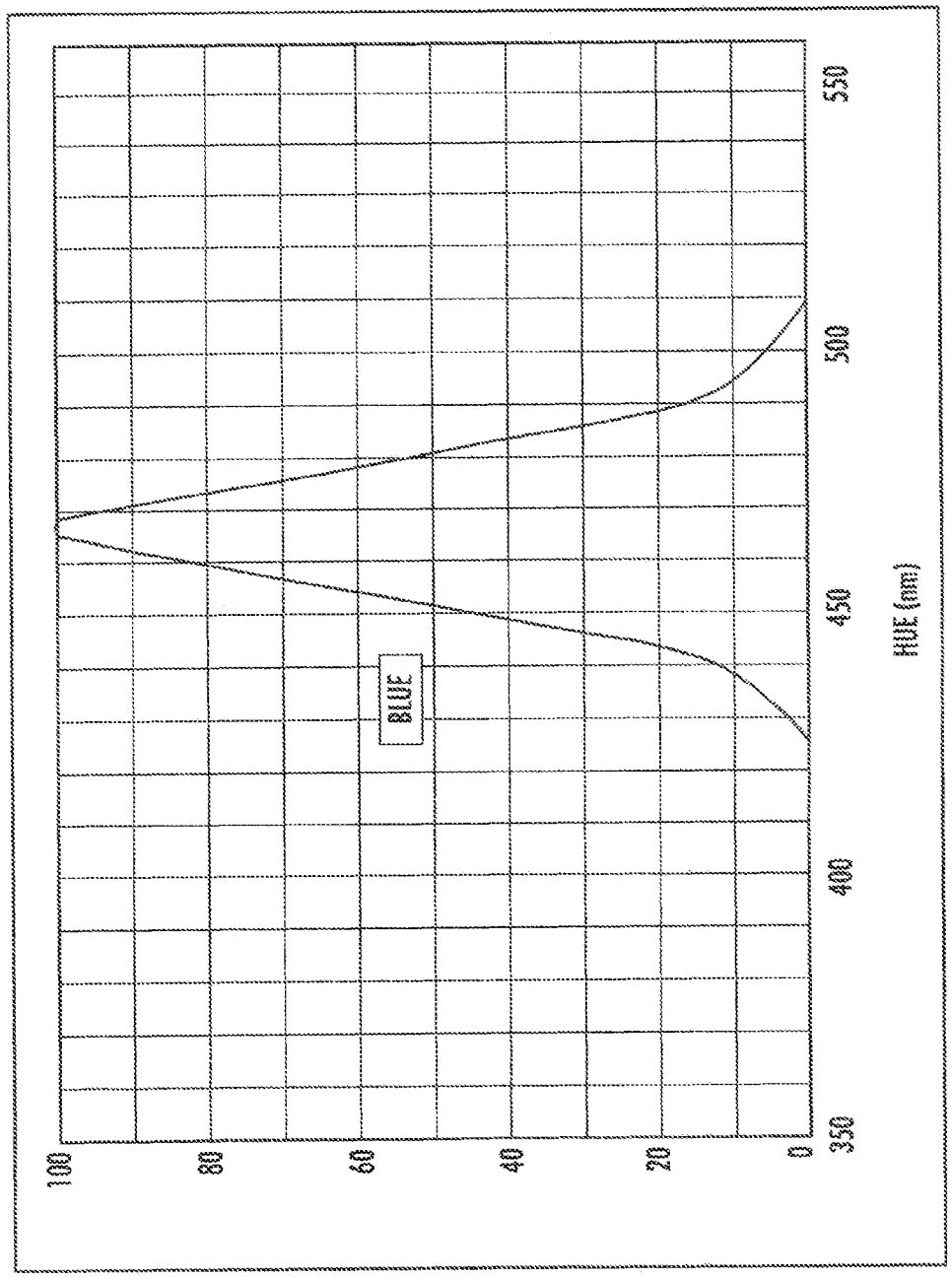
FIG. 3 is a chart depicting the wavelength of the output of LEDs of an embodiment of the present invention.

FIG. 3 is a graph of the light wavelength output of the blue 5 watt 50 lumen LEDs used in one embodiment of this invention.

LED replacement using the method and system of the present invention will add longevity to the FLIPR readers and has been discovered to increase the time between light related refurbishment since when using the system of the present invention refurbishment times between work increases dramatically. Accordingly, the results achieved with the present invention not only provide a quick and easy way to refurbish a FLIPR machine they surprisingly add longevity to the readers and provide a result not anticipated with LED use in a refurbishment situation.

Nothing in the embodiments is designed to be limiting unless otherwise stated. In view of the disclosure of the embodiments once can easily see if skilled in the art other substitutions of filters support materials LEDs and the like, within the scope of the present invention. The claims which follow should not therefore be read as so limiting.

What is claimed is:

1. A method for repairing a fluorescence microplate reader having a water cooled laser light source that has been removed from the reader comprising:
   a) selecting one or more LED lights having a total lumen output sufficient to produce a replacement lumen output, the LED lights mounted in a rigid holder and the holder mounted on a support;
   b) providing a light filter in front of the one or more LED lights to change a light output to a desired wavelength;
   c) positioning the support in the reader such that the light from the one or more LED lights shines on the bottom of a microplate positioned in the reader ; and
   d) connecting the one or more LED lights to the reader such that they operate in place of the laser light.

2. A method for repairing a microplate reader according to claim 1 wherein the LED lights are positioned to shine on the bottom of the microplate at an angle of less than 90 degrees.

3. A method for repairing a microplate reader according to claim 1 wherein the LED lights are positioned to shine on the bottom of the microplate at an angle of 90 degrees.

4. A method for repairing a microplate reader according to claim 3 wherein the light from the LED lights reflects off of at least one mirror before reaching the bottom of the microplate.

5. A method for repairing a microplate reader according to claim 4 wherein there is a dichroic mirror positioned at an angle to reflect the LED light to the bottom of the microplate and pass fluorescence coming from the bottom of the microplate through the dichroic mirror.

6. A method for repairing a microplate reader according to claim 1 wherein the LED lights are enclosed in a case.

7. A method for repairing a microplate reader according to claim 1 wherein there is one or more pieces of dark material placed beneath a microplate holder in the microplate reader positioned to reduce reflective light from the LED lights.

8. A method according to claim 1 wherein the LED lights, and support are attached as a single unit which can be place in the reader.

9. A method according to claim 1 wherein further comprising a dichroic filter for reflecting filtered light from the LED lights to the bottom of the microplate when the support is positioned within the reader.

10. A method according to claim 1 herein the LED's are sufficient to reach 10000 RFU at 0.05 sec exposure during a yellow plate test.

11. A method according to claim 1 wherein a lumen intensity is modified and homogenized by either a filter or a light reducing aperture.

12. A method according to claim 1 wherein a lumen intensity of the LEDs is at least about 200 lumens.

13. A method according to claim 1 wherein a lumen intensity of the LEDs is about 300 lumens.

14. A method according to claim 1 wherein the LEDs emit light in a wavelength from about 425 to about 510 nanometers.

15. A method according to claim 1 wherein the LEDs emit a maximum light out at a wavelength of about 475 nanometers.

16. A method according to claim 1 wherein there are 6 LEDs each having a lumen output of about 50 lumens.

17. A method according to claim 1 wherein the LEDs are high power LEDs.

* * * * *